US006554771B1

United States Patent
Buil et al.

(10) Patent No.: US 6,554,771 B1
(45) Date of Patent: Apr. 29, 2003

(54) POSITION SENSOR IN ULTRASOUND TRANSDUCER PROBE

(75) Inventors: Vincentius Paulus Buil, Eindhoven (NL); Paul R. Detmer, Seattle, WA (US); Jing-Ming Jong, Seattle, WA (US); Xiang-Ning Li, Mill Creek, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/026,585

(22) Filed: Dec. 18, 2001

(51) Int. Cl.[7] .................................. A61B 8/14
(52) U.S. Cl. .................. 600/459; 600/443; 600/424
(58) Field of Search ................. 600/437–472, 600/424

(56) References Cited

U.S. PATENT DOCUMENTS 5,127,409 A * 7/1992 Daigle ..................... 600/443
5,335,663 A * 8/1994 Oakley et al. ............ 600/459
6,275,724 B1 * 8/2001 Dickinson et al. ........ 600/424
2002/0120197 A1 * 8/2002 Kleffner et al. ........... 600/459

* cited by examiner

Primary Examiner—Marvin M. Lateef
Assistant Examiner—Ruby Jain
(74) Attorney, Agent, or Firm—W. Krinton Yolks, Jr.

(57) ABSTRACT

An ultrasound imaging system (1) comprises a transducer probe (2) for supplying ultrasound waves to a subject area (A), for receiving ultrasound waves reflecting from the subject area (A), and for converting the reflecting waves into a first electrical signal, at least one position sensor (3) provided in the transducer probe (2) for detecting positional information on the transducer probe (2) relative to the subject area (A) during operation, and for generating a second electrical signal corresponding to the detected positional information, a processing unit (41) for controlling the transducer probe (2) and for processing the first and second electrical signals into an image. The position sensor (3) comprises a unit (23) for optically acquiring images of a surface of the subject area (A) during operation, for acquiring information from said images, and for processing said information into positional information on the transducer probe (2) relative to the subject area (A).

Figure 1:
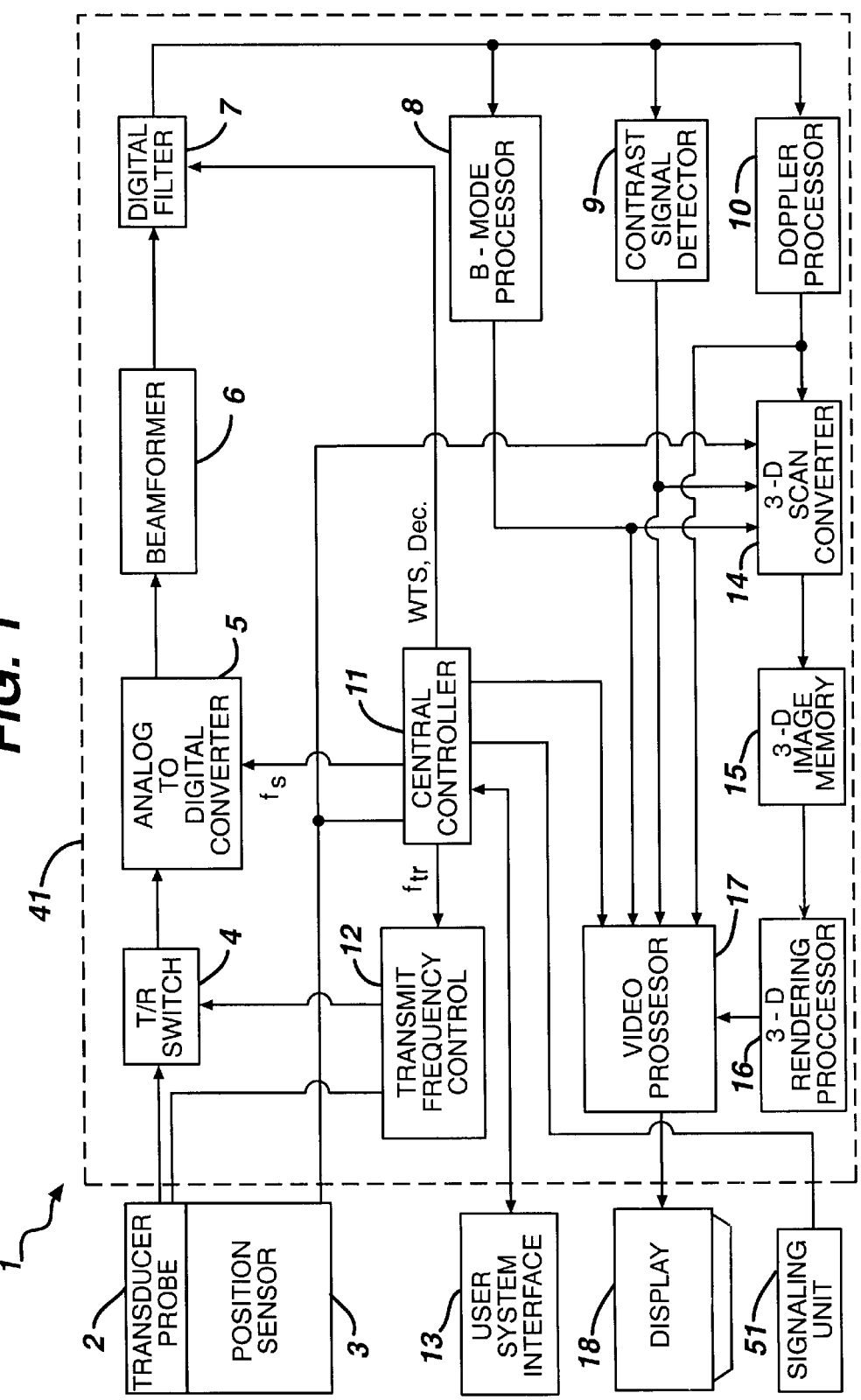

An improved ultrasound imaging system is provided which offers more accurate position detection.

6 Claims, 3 Drawing Sheets

POSITION SENSOR IN ULTRASOUND TRANSDUCER PROBE

The invention relates to an ultrasound imaging system comprising a transducer probe for supplying ultrasound waves to a subject area, for receiving ultrasound waves reflecting from the subject area, and for converting the reflecting waves into a first electrical signal, at least one position sensor provided in the transducer probe for detecting positional information on the transducer probe relative to the subject area during operation, and for generating a second electrical signal corresponding to the detected position, a processing unit for controlling the transducer probe and for processing the first and second electrical signals into an image.

Ultrasound imaging systems are commonly used to generate two-dimensional diagnostic images of internal features of a patients body. During operation the transducer is positioned on a surface of a subject area on a patients body and emits ultrasound waves. The ultrasound waves propagate into the subject area and are in part absorbed, dispersed, refracted and reflected by internal structures. The reflecting ultrasound waves are received back by the transducer probe, and are converted into electronic signals which are processed by the system into a two-dimensional image which can be used for diagnostic purposes.

Next to two-dimensional imaging, in recent years systems have been developed which are capable of three-dimensional ultrasound imaging. Three-dimensional imaging allows a better view of the organ being examined, and is for example especially suitable for visualization of a foetus and for early detection of tumors. To obtain such a three-dimensional ultrasound image, it is necessary to scan a volume instead of a two-dimensional plane. One way to realize this is to sequentially acquire two-dimensional slices of the subject area as described above, while detecting positional information on the transducer probe relative to the subject area by means of a position sensor during acquisition of the slices. This information on the changing position of the transducer during acquisition of the slices is then processed by the system into information on the position of each slice relative to the others, to combine the two-dimensional slices into a three-dimensional image. An ultrasound diagnostic imaging system as described in the opening paragraph is known from U.S. Pat. No. 5,127,409. In this system the position sensor comprises a number of ultrasound transducers for obtaining Doppler wave signals, which are provided in a part of the transducer probe which contacts the surface of the subject area during operation. The Doppler wave signals obtained by the ultrasound transducers are processed by the system into an estimation of the velocity of the transducer probe. By integrating the velocity over time, the translational and rotational characteristics of the position of the transducer probe relative to the subject area are then established.

A drawback of the known system is that the position sensor principally measures velocity. In order to obtain the positional information on the transducer probe, the velocity signals must be integrated over time. Any noise occurring during the period in which the transducer probe has been moving and the Doppler wave signals have been obtained, is also integrated which leads to large offset errors that cannot be easily predicted or corrected. This damages the accuracy of the positional information on the transducer probe and thus also the correct composition of the two-dimensional slices into a three-dimensional image.

It is an object of the invention to provide an improved ultrasound imaging system which offers more accurate position detection.

To achieve this object, an ultrasound imaging system according to the invention is characterized in that the position sensor comprises a unit for optically acquiring images of a surface of the subject area during operation, for acquiring information from said images, and for processing said information into positional information on the transducer probe relative to the subject area. By optically acquiring images of the surface of a subject area, being the skin surface of a patient, and thus acquiring information regarding the position of the transducer probe relative to the subject area, the acquisition of positional information is much less sensitive to noise occurring during movement of the transducer probe. The optical path between the scanned skin surface and the unit in the transducer probe is relatively short and is not easily disturbed. This enhances the accuracy of the detected position of the transducer probe and thus also the quality of the three-dimensional ultrasound image resulting from a composition of two-dimensional slices based on said positional information.

An embodiment of an ultrasound imaging system according to the invention is characterized in that the acquisition of information from said images comprises determination of a recognizable element in a first image, determination of the position of said element on the image, and mutual comparison of the positions of said element on further successively taken images. The information on the changes of the position of the element across successively taken images is relatively insensitive to noise and thus can advantageously be used to be processed into accurate positional information on the transducer probe relative to the subject area.

It is advantageous when the positional information on the transducer probe, which is provided by the unit, comprises translational and rotational information. The translational information is used by the system to determine the direction and the velocity of the transducer probe. When the direction of the transducer probe is known, the system has input on how to place the incoming two-dimensional slices with respect to each other in order to obtain a correct three-dimensional image. In this manner erroneous inversions are avoided. When the velocity of the transducer probe is known, the system is able to check whether this velocity is not too high. When the transducer probe is moved too fast across the subject area, certain slices are liable to be not properly scanned which would disturb the creation of a correct three-dimensional image. The rotational information is used by the system to determine whether any turns of the transducer probe occur which should be taken into account during the construction of a three-dimensional ultrasound image on the basis of the two-dimensional slices.

An embodiment of an ultrasound imaging system according to the invention is characterized in that the unit comprises illuminating elements, a lens system, an image sensor, and a digital signal processor. The illuminating elements provide the surface of the subject area with light, the light is scattered by the surface structure of the subject area, and this scattered light is focussed by the lens system. The image sensor takes repeated images of the pattern of light which is scattered from the surface of the subject area. By comparing successively taken images and determining the positions of identical regions of the scattered patterns on these images, the unit determines the positional changes of the transducer probe relative to the subject area during the scanning of the two-dimensional ultrasound slices. This information on the changing positions of the transducer probe relative to the subject area is then used by the system to construct a three-dimensional ultrasound image on the basis of the two-dimensional images of the slices. This unit can be manufactured against relatively low costs, and can be provided in the transducer probe in a relatively inexpensive manner. This benefits the cost-effectiveness of the whole system.

An embodiment of an ultrasound imaging system according to the invention is characterized in that at least two position sensors are provided. With two position sensors, the results of the measurement of translation of these sensors can be processed into an even more accurate determination of the rotation of the transducer probe relative to the subject area.

A further embodiment of an ultrasound imaging system according to the invention is characterized in that the processing unit is arranged to provide a warning signal dependent on the positional information. In this manner the system can warn the operator during handling of the transducer probe for any handling errors which might harm the acquisition of a correct three-dimensional image, such as a scanning velocity which is too high, or an unwanted degree of rotational movement of the transducer probe.

Figure 2A:
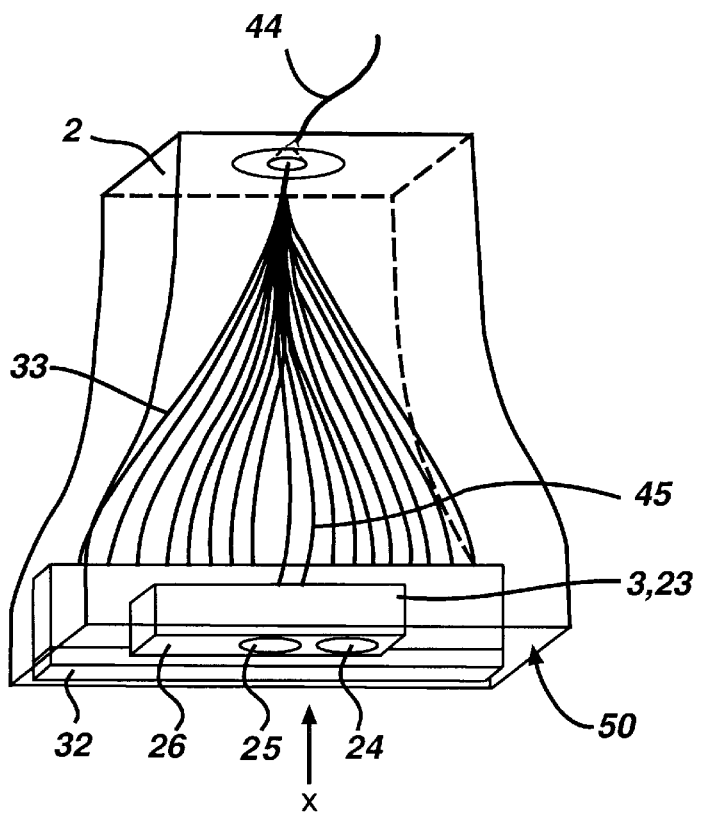
Figure 2B:
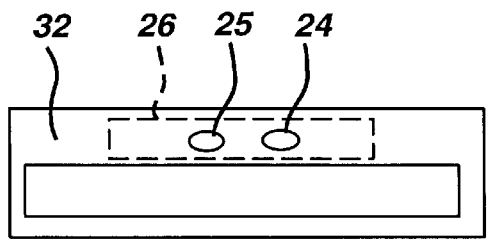
Figure 3:
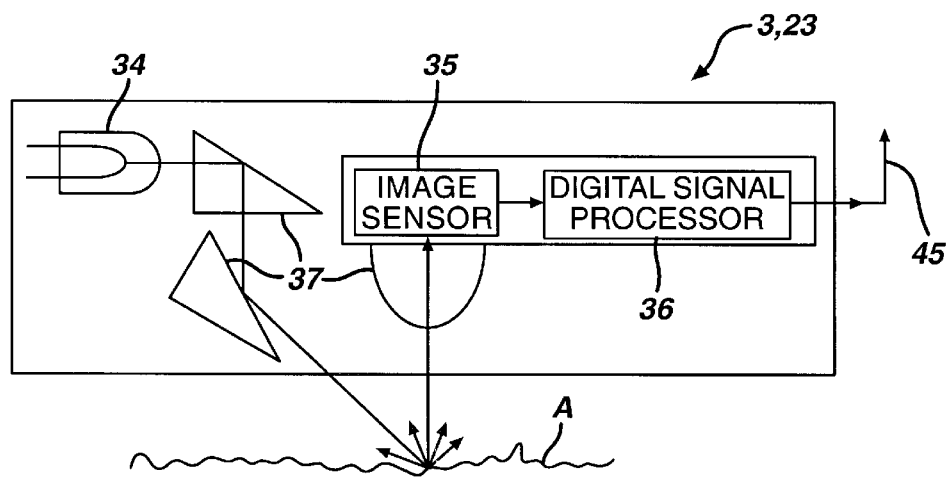
Figure 4A:
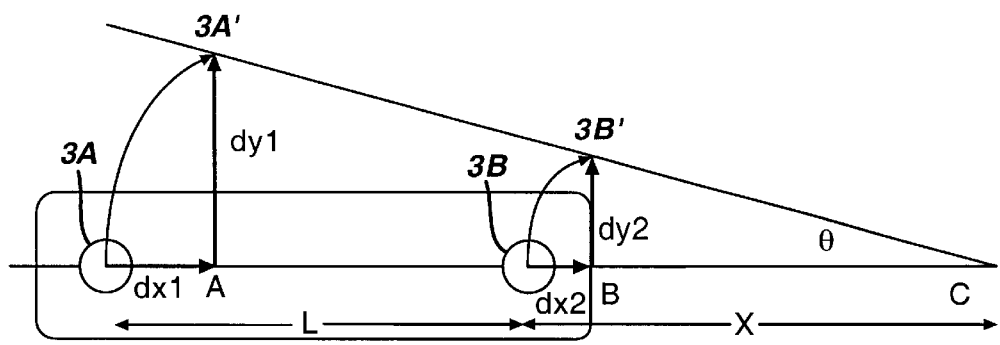
Figure 4B:
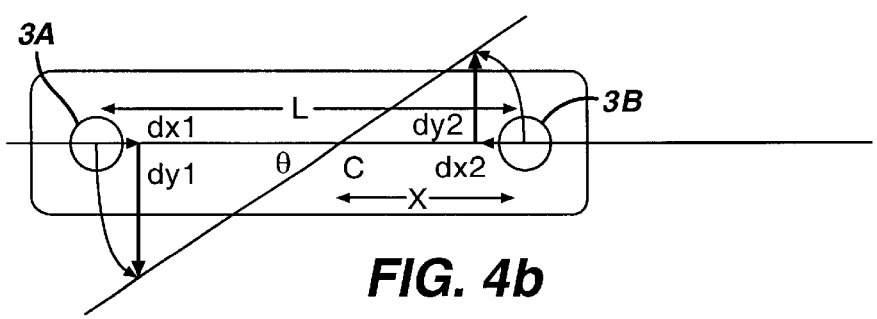

The invention will be described in more detail hereinafter with reference to the drawings, in which FIG. 1 shows in block diagram form a first embodiment of an ultrasound imaging system according to the invention, FIGS. 2a and 2b are respectively a perspective transparent view, and a view from direction X, of a transducer probe of a first embodiment of an ultrasound imaging system according to the invention, FIG. 3 shows a detail of a position sensor in the transducer probe of FIG. 2, and FIGS. 4a and 4b show a detail of a transducer probe of a further embodiment of an ultrasound imaging system according to the invention, in a view from the direction X of FIG. 2b.

FIG. 1 shows a block diagram of a first embodiment of an ultrasound imaging system according to the invention. Said system 1 comprises a transducer probe 2 for supplying ultrasound waves to a subject area and for receiving ultrasound waves reflecting from the subject area, and for converting the reflecting waves into a first electrical signal. The transducer probe 2 further comprises a position sensor 3 for detecting positional information on the transducer probe 2 relative to the subject area during operation, and for generating a second electrical signal dependent on that positional information. The position sensor 3 comprises a unit 23 provided in the transducer probe 2 for optically acquiring images of a surface of the subject area A during operation, for acquiring information from said images, and for processing said information from the acquired images into positional information on the transducer probe 2 relative to the subject area A. The configuration of the transducer probe 2 and the position sensor 3 in this embodiment is further described hereinafter on the basis of FIG. 2.

The system 1 further comprises a processing unit 41 for controlling the transducer probe 2 and for processing the first and second electrical signals into an image. In this embodiment, the processing unit 41 comprises a central controller 11 for commanding a transmit frequency control 12 to transmit a desired transmit frequency band via the transducer probe 2. The parameters of the transmit frequency band, $f_{tr}$, are coupled to the transmit frequency control 12, which causes the transducer probe 2 to transmit ultrasonic waves in the fundamental frequency band. It will be understood, of course, that any ultrasonic frequency may be used, depending on the desired depth of penetration and the sensitivity of the transducer and ultrasonic system. In this embodiment the transducer probe 2 comprises an array 32 of discrete elements, comprising piezoelectric crystals. It is noted however that other types of transducers may be used, such as MEMS (micro-electric-mechanical system).

The transducer probe 2 supplies ultrasound waves to a subject area, receives ultrasound waves reflecting from the subject area, and converts the reflecting waves into a first electrical signal. The controller 11 responds to commands from an operator entered via a user system interface 13 that includes an interface program and a mouse, keyboard, or other input device for conveying instructions to the central controller 11. The first electrical signal received from the transducer probe 2 is presented to a transmit/receive (T/R) switch 4 and digitized by an analog-to-digital converter 5. The sampling frequency $f_s$ of the A/D converter is controlled by the central controller 11. The desired sampling rate dictated by sampling theory is at least twice the highest frequency $f_c$ of the received echoes. Sampling rates higher than the minimum requirement can also be used. The signal sample is delayed and summed by a beamformer 6 to form a coherent echo signal. The coherent echo signal is then filtered by a digital filter 7 to a desired passband. The digital filter 7 can also shift the frequency band to a lower or baseband frequency range.

The characteristics of the digital filter 7 are controlled by the central controller 11, which provides the filter with multiplier weights (Wts) and decimation (Dec.) control. From the digital filter 7, the filtered signal is detected and processed by a B-mode processor 8, a contrast signal detector 9, or a Doppler processor 10. The Doppler processor 10 applies conventional Doppler processing to the echo signal to produce velocity (Vel) and power (Pwr) Doppler signals. The outputs of the processors 8 and 10 and contrast signal detector 9 are coupled to a video processor 17 which displays these outputs as a two-dimensional ultrasonic image on the display 18.

The outputs of the two processors 8 and 10 and contrast signal detector 9 are also coupled to a three-dimensional scan converter 14. This scan converter 14 generates, in combination with a second electrical signal corresponding to the detected position of the transducer probe relative to the subject area as generated by the position sensor 3, a three-dimensional ultrasonic volume data set that is stored in the 3D image memory 15. The 3D image rendering processor 16 processes the three-dimensional volume data into two-dimensional slice images of the volume or volume-rendered three-dimensional views of the volume, which are provided to the video processor 17 so they can be displayed. Three-dimensional rendering may be performed using a variety of conventional techniques.

In this embodiment, an operator can select among the outputs of the contrast signal detector 9 and the processors 8 and 10 for two- or three-dimensional display of an ultrasonic image. Furthermore, in this embodiment the processing unit 41 is arranged to provide a warning signal dependent on the positional information of the unit 23. The central controller 11 monitors, based on the positional information of the unit 23, whether the velocity and direction of the movement of the transducer probe 2 is adequate for acquiring and assembling accurate ultrasound volume data. When the velocity is too high or unwanted rotations of the transducer probe 2 relative to the subject area occur, certain slices are liable to be not properly scanned which would affect the correct construction of a three-dimensional image.

When the central controller detects an incorrect velocity or rotation, it warns the operator via a signalling unit 51, for example with an audio signal. It is to be understood that other warning signals can be used, such as optical signals, display icons or combinations of warning signals. In this manner the operator is able to correct the handling of the transducer probe 2 during acquisition of the ultrasound images. It is noted that, next to the embodiment as described above, the processing unit 41 may comprise other known types of configuration.

FIGS. 2a and 2b show the transducer probe 2 of a first embodiment of an ultrasound imaging system according to the invention in more detail. The transducer probe 2 comprises the position sensor 3 and the array 32 of discrete elements that transmit ultrasound waves and receive ultrasound waves reflecting from the subject area A. In this embodiment the array 32 of piezoelectric crystals is connected via array signal wires 33 with a transducer probe cable 44, via which the transducer probe is connected with the system 1. The position sensor 3 comprises a unit 23 for optically acquiring images of a surface of the subject area A during operation, for acquiring information from said images, and for processing said information from the acquired images into positional information on the transducer probe 2 relative to the subject area A. Said unit 23 is connected via position signal wires 45 to the transducer probe cable 44.

As can be seen in FIGS. 2a and 2b, the elements 24, 25 on the side 26 of said unit 23 which opposes the subject area A and optically acquire images of the surface of the subject area A are provided in a part 50 of the transducer probe 2 which contacts the surface of the subject area A during operation. In this manner the optical path between the scanned skin surface and these elements is very short and is not easily disturbed.

FIG. 3 shows the unit 23 in the transducer probe 2 of FIGS. 2a and 2b in more detail. In this embodiment the unit 23 comprises illuminating elements 34, here formed by Light Emitting Diode (LED), a lens system 37, formed by prisms and a lens, a image sensor 35, here formed by a CCD-camera, and a digital signal processor 36. This is a cost-effective configuration of the unit 23 which can be incorporated into the transducer probe 2 in a relatively inexpensive way. During operation, the transducer probe 2 is moved across a surface of a subject area. Light originating from the LED follows a light path indicated by arrows in FIG. 3 via the prisms and illuminates said surface of the subject area. The light is scattered by the surface structure of the subject area, and this scattered light is focussed by the lens. The digital camera 35 then acquires a microscopic image of the pattern of light which is scattered from the surface of the subject area, which image is processed by the digital signal processor 36. These images are acquired successively during the movement of the transducer probe 2 across the subject area. The acquisition of positional information from said images comprises determination of a recognizable element in a first image, which in this embodiment comprise a recognizable region of a scattered pattern of light. The digital signal processor 36 determines the position of said element on the image, and then mutually compares the positions of said element on further successively taken images.

By comparing successively taken images and determining the positions of identical regions of the scattered patterns on these images, the digital signal processor 36 determines positional changes of the transducer probe 2 relative to the subject area during the acquisition of the two-dimensional ultrasound slices. Based on this information on the changing positions of the transducer probe 2 relative to the subject area, the digital signal processor 36 provides the three-dimensional scan converter 14 with information on the position of the transducer probe 2 during the acquisition of the two-dimensional sets of slices via the position signal wires 45. This information on the varying positions of the transducer probe 2 is then used by the three-dimensional scan converter 14 to construct a three-dimensional image out of the two-dimensional slices. The information on the changes of the position of the element across successively taken images is relatively insensitive to noise and thus can advantageously be used to be processed into accurate positional information on the transducer probe relative to the subject area.

In stead of only one position sensor, also two or even more position sensors may be provided. With two position sensors, the results of the measurement of translation of these sensors can be processed into an even more accurate determination of the rotation of the transducer probe relative to the subject area. This is shown in relation to FIGS. 4a and 4b. These Figures show a detail of the transducer probe 2' of a further embodiment of an ultrasound imaging system according to the invention, in a view from a direction X, similar to the view of FIG. 2b. In FIG. 4a, two position sensors 3A and 3B according to the invention are separated by a distance L. The transducer probe 2 is rotated by a small angle $\theta$ which is exaggerated in the figure. It is assumed that 3A translates by (dx1, dy1), and 3B translates by (dx2, dy2). Because the transducer probe is a rigid body, |3A3B|= |3A'3B'|=. The center of rotation C is a distance X from sensor 3B. Based on the fact that $\triangle$CA3A' $\square$ $\triangle$CB3B', the distance X can be computed from X–dx2/L+X–dx1=dy2/dy1, and the rotation angle $\theta$=Tan$^{-1}$(dy2/X–dx2). The center of rotation may also lie between the two sensors, as shown in FIG. 4b. In this case, the distance X can be computed from X–dx2/L–X–dx1=dy2/dy1, and the rotation angle $\theta$=Tan$^{-1}$ (dy2/X–dx2).

By optically acquiring images of the skin surface of a patient and thus acquiring information regarding the position of the transducer probe relative to the subject area, the patient him- or herself becomes the reference system for the positional information. Any movements of the patient thus do not disturb the acquirement of correct positional data on the transducer probe 2 by the unit 23, since the data are acquired directly at the surface of the skin and the transducer probe 2 is moved along with any movement of the patient. If the patient moves and the transducer probe 2 does not move along, the unit 23 will detect a deviation in the acquired images of the skin surface and will correct the positional information for this motion. Furthermore the optical path between the scanned skin surface and the unit 23 is very short. This is advantageous since in this manner the optical path is not easily disturbed. The operator can thus freely move the transducer probe 2 and the patient can be positioned in a comfortable body orientation during scanning.

Furthermore, it is common practice that the surface of the subject area to be scanned is provided with a gel to acoustically couple the transducer probe 2 and the subject area to be scanned. The unit 23 can be easily used in combination with this gel, since its operation is not influenced by the gel.

It is furthermore noted, that the processing unit being arranged to provide a warning signal dependent on the positional information, as described before, in itself is also advantageously usable in other ultrasound imaging systems in which the at least one position sensor 3 comprising a unit 23 provided in the transducer probe 2 for optically acquiring images of a surface of the subject area A during operation, for acquiring information from said images, and for processing said information from the acquired images into positional information on the transducer probe 2 relative to the subject area A, is not provided. The positional information then may also be acquired by other types of position sensors.

What is claimed is:

1. An ultrasound imaging system (1) comprising:
   a transducer probe (2) having an ultrasonic transducer for supplying ultrasound waves to a subject area (A), for receiving ultrasound waves reflecting from the subject area (A), and for converting the reflecting waves into a first electrical signal,
   at least one optical position sensor (3) provided in the transducer probe (2) for detecting positional information on the transducer probe (2) relative to a surface of the subject area (A) during operation, and for generating a second electrical signal corresponding to the detected positional information,
   a processing unit (41) for controlling the transducer probe (2) and for processing the first and second electrical signals into an image,
   wherein the position sensor (3) comprises a unit (23) for optically acquiring images of a surface of the subject area (A) during operation, for acquiring information from said subject surface images, and for processing said information into positional information on the transducer probe (2) relative to the subject area (A).

2. A system according to claim 1, wherein the acquisition of information from said images comprises determination of a recognizable element having a position in a first image, determination of the position of said element on the image, and mutual comparison of the positions of said element on further successively taken images.

3. A system according to claim 1, characterized in that said positional information on the transducer probe (2) comprises translational and rotational information.

4. An ultrasound imaging system (1) comprising:
   a transducer probe (2) for supplying ultrasound waves to a subject area (A), for receiving ultrasound waves reflecting from the subject area (A), and for converting the reflecting waves into a first electrical signal,
   at least one position sensor (3) provided in the transducer probe (2) for detecting positional information on the transducer probe (2) relative to the subject area (A) during operation, and for generating a second electrical signal corresponding to the detected positional information,
   a processing unit (41) for controlling the transducer probe (2) and for processing the first and second electrical signals into an image,
   wherein the position sensor (3) comprises a unit (23) for optically acquiring images of a surface of the subject area (A) during operation, for acquiring information from said images, and for processing said information into positional information on the transducer probe (2) relative to the subject area (A), and
   wherein the unit (23) comprises illuminating elements (34), a lens system (37), an image sensor (35), and a digital signal processor (36).

5. A system according to claim 1, characterized in that at least two optical position sensors (3*a*, 3*b*) are provided.

6. A system according to claim 1, characterized in that the processing unit(41) is arranged to provide a warning signal dependent on the positional informational.

\* \* \* \* \*